US005451789A

United States Patent [19]
Wong et al.

[11] Patent Number: 5,451,789
[45] Date of Patent: Sep. 19, 1995

[54] HIGH PERFORMANCE POSITRON CAMERA

[75] Inventors: Wai-Hoi Wong, Houston; Keri Hicks, Sugarland, both of Tex.

[73] Assignee: Board of Regents, The University of Texas System, Austin, Tex.

[21] Appl. No.: 94,409

[22] Filed: Jul. 19, 1993

[51] Int. Cl.$^6$ .............................................. G01T 1/164
[52] U.S. Cl. ........................ 250/363.03; 250/363.04; 250/363.1; 378/37
[58] Field of Search ...................... 250/363.03, 363.04, 250/363.10; 378/37

[56] References Cited

U.S. PATENT DOCUMENTS

| | | | |
|---|---|---|---|
| 4,647,799 | 3/1987 | Hsu et al. | 307/455 |
| 4,733,083 | 3/1988 | Wong | 250/368 |
| 4,883,966 | 11/1989 | Wong | 250/363.02 |
| 5,030,830 | 7/1991 | Okada | 250/363.03 |
| 5,252,830 | 10/1993 | Weinberg | 378/37 |
| 5,291,021 | 3/1994 | Tanaka et al. | 250/363.03 |

FOREIGN PATENT DOCUMENTS

61-83984  4/1986  Japan .

OTHER PUBLICATIONS

Williams et al, "Design of the Neuro-ECAT: A High Resolution, High Efficiency Positron Tomograph for Imaging the Adult Head or Infant Torso", IEEE Trans. Nucl. Sci., NS-28 (2), Apr. 1981, pp. 1736-1740.

Kuhl, D. E., Clinical PET, "Today, Tomorrow, or Never," The Eighth Annual Society of Nuclear Medicine Lectureship, *J. Nucl. Med.* 32(5):909 (1991).

Wagner, H. N., "Clinical PET, Its Time has Come," *J. Nucl. Med.* 32(4):561–564 (1991).

Strauss, L. G. and Conti, P. S., "The Applications of PET in Clinical Oncology," *J. Nucl. Med.*, 32:623–648 (1991).

Coleman, R. E., et al., "Clinical Application of PET for the Evaluation of Brain Tumors," *J. Nucl. Med.*, 32(4):616–622 (1991).

Martiat, P., et al., "In Vivo Measurement of Carbon-11 Thymidine Uptake in Non-Hodgkin's Lymphoma Using Positron Emission Tomography," *J. Nucl. Med.*, 29(10):1633–1637 (1988).

Guerrero, T. M., et al. "Characterization of a Whole Body Imaging Technique for PET," *IEEE Trans. Nucl. Sci.,* 37(2):676–680 (1990).

Hoh, C. K., et al., "PET Total Body Imaging of Breast Cancer with FDG and F-18 Ion," *J. Nucl. Med.*, 32(5):981–982 (1991).

Wahl, R. L., et al., "Primary and Metastatic Breast Carcinoma: Initial Clinical Evaluation with PET with the Radiolabeled Glucose Analogue 2-[F-18]--Fluoro-2-deoxy-D-glucose$^1$," *Radiology,* 179:765–770 (1991).

Hoh, C. K., et al. "Total Body PET Imaging of Tumors of the Abdomen and Pelvis with FDG," *J. Nucl. Med.*, 32(5):982 (1991).

Wong, W. H., et al., "Image Improvement and Design Optimization of the Time-of-Flight PET," *J. Nucl. Med.* 24:52–60 (1983).

Wong, W. H. et al., "Characteristics of Small Barium Fluoride (BaF$_2$) Scintillator for High Intrinsic Resolution Time-of-Flight Positron Emission Tomography,"

(List continued on next page.)

*Primary Examiner*—Carolyn E. Fields
*Attorney, Agent, or Firm*—Arnold, White & Durkee

[57] ABSTRACT

The invention relates to methods and apparatus for cameras for gamma radiation, including cameras for positron emission tomography (PET). Included in the invention are cameras having radiation detector arrays splittable into sections, which then may be used to extend the axial field-of-view in a two-dimensional mode. Individual array sections may be equipped with collimators. Additionally, splittable PET cameras having detector arrays approximately one-fourth the diameter of conventional whole-body PET cameras are disclosed as having insertable conformal collimators comprising stacks of planar rings. The inner contours of the planar rings are adapted to accept objects to be imaged in the camera and to closely conform to the objects' surface contours.

27 Claims, 5 Drawing Sheets

OTHER PUBLICATIONS

*IEEE Trans. Nucl. Sci.,* vol. NS-31, pp. 381-386 (1984).

Wong, W. H., "PET Camera Performance Design Evaluation for BGO and BaF$_2$ Scintillators (Non-Time-of-Flight)," *J. Nucl. Med.* 29(3):338-347 (1988).

Bendriem, B., et al., "Analysis of Scatter Deconvolution Technique in PET Using Monte Carlo Simulation," *J. Nucl. Med.,* 28(4):681 (1987).

Wong, W. H., "Designing a Stratified Detection System for PET Cameras," *IEEE Trans. Nucl. Sci.,* 33(1):591-596 (1986).

Wong, W. H., et al., "A Slanting Light-Guide Analog Decoding High Resolution Detector for Positron Emission Tomography Camera," *IEEE Trans. Nucl. Sci.,* vol. NS-34, pp. 280-284 (1987).

Wong, W. H. et al., "A Simple High Resolution PET Camera Detector Design—Crystal Masking Analog Positioning with High Optical Efficiency," *J. Nucl. Med.,* 29(5):761 (1988).

Chang, W., et al., "A Multi-Detector Cylindrical SPECT System for Phantom Imaging," Conference Record, *IEEE Nucl. Science Symposium,* pp. 1208-1211 (1990).

Digby, W. M. et al., "Detector, Shielding and Geometric Design Factors for a High-Resolution PET System," *IEEE Trans. Nucl. Sci.,* 37(2):664-760 (1989).

Dale, S. and Bone, D. "Tomography Using a Rotating Slant-Hole Collimator and a Large Number of Projections," *J. Nucl. Med.,* 31(10):1675-1681 (1990).

Dale, S. and Bone, D., "Thallium-201 Myocardial Tomography with a Rotating Slant-hole Collimator and Large Number of Projections," *J. Nucl. Med.,* 31(10):1682-1687 (1990).

Barret, H., Editorial: "Limited-Angle Tomography for the Nineties," *J. Nucl. Med.,* 21(10):1688-1692 (1990).

Wallis, C., "A Puzzling Plague," *Time Magazine,* Jan. 14, 1991, pp. 49-52 (1991).

Visscher, D. W., et al., "Prognostic Significance of Morphological Parameters and Flow Cytometric DNA Analysis in Carcinoma of the Breast," *Pathology Annual 1990,* 25 pt. 1:171-210 (1990).

Rozental, J. M., "Changes in Glucose Uptake by Malignant Gliomas: Preliminary Study of Prognostic Significance," *J. Neuro-Oncol.,* 10:75-83 (1991).

Martiat, P. et al., "In Vivo Measurement of Carbon-11 Thymidine Uptake in Non-Hodgkin's Lymphoma Using Positron Emission Tomography," *J. Nucl. Med.,* 29(10):1633-1637 (1988).

Wahl, R. L., "Active Breast Cancer Chemohoromonotherapy Sequentially Assessed by FDG PET: Early Metabolic Decrements Precede Tumor Shrinkage," *J. Nucl. Med.,* 32(5):982 (1991).

Derenzo, S. E., et al., "Imaging Properties of a Positron Tomograph with 280 BGO Crystals," *IEEE Trans. Nucl. Sci.,* vol. NS-28(1):81-89 (1981).

Derenzo, S. E., et al., "Analytical Study of a High Resolution Positron Ring Detector System for Transaxial Reconstruction Tomography," *J. Nucl. Med.,* 16(12):1116-1173 (1975).

Muehllehner, G. et al., "A Hexagonal Bar Positron Camera: Problems and Solutions," *IEEE Trans. Nucl. Sci.,* vol. NS-30(1):652-660 (1983).

Karp, J. S., et al., "Event Localization in a Continuous Scintillation Detector Using Digital Processing," *IEEE Trans. Nucl. Sci.,* 33(1):550-555 (1986).

Karp, J. S., et al. "Continuous-Slice PENN-PET: A Positron Tomograph with Volume Imaging Capability," *J. Nucl. Med.,* 31(5):617-627 (1990).

Lewellan, T. K., et al. "Evaluation of a Clinical Scintillation Camera with Pulse Tail Extrapolation Electronics," *J. Nucl. Med.,* 30(9):1554-1558 (1989).

Karp, J. S., et al., "Performance Standards in Positron Emission Tomography," *J. Nucl. Med.,* 32(12):2342-2350 (1991).

Townsend, D., et al., "A Rotating PET Camera Using BGO Block Detectors," *Conference Record of the 1991 IEEE Nuclear Science Symposium and Medical Imaging Conference,* pp. 1658-1662 (Nov. 1991).

Dahlbom, M., et al., "Whole-Body Positron Emission Tomography: Part I. Methods and Performance Characteristics," *J. Nucl. Med.,* 33(6):1191-1199 (1992).

HIGH PERFORMANCE POSITRON CAMERA

BACKGROUND OF THE INVENTION

1. Field of the Invention

The invention relates to methods and apparatus for cameras sensitive to gamma radiation.

2. Background

Gamma radiation is produced by the nuclei of certain radioactive atoms during annihilation of positrons by electrons. Cameras sensitive to gamma radiation are used to identify and locate sources of gamma radiation in the vicinity of the camera.

Gamma radiation may be produced in a human or animal by injecting certain isotopes (radionuclides) which decay by emission of positrons. Cameras with gamma radiation detectors arranged in circular or cylindrical arrays may be placed around a human or animal subject to locate areas of concentration of the injected isotopes within the animal or human body. This is positron emission tomography (PET). Analogous equipment and procedures can be used to locate isotopes within inanimate objects when the isotopes decay by emission of positrons.

Throughout this application, "PET camera" and similar terms will be understood to include cameras sensitive to gamma radiation from any source within the object field of the camera.

PET Applications in Oncology

Oncology is becoming a very important area of clinical PET application. The strengths of positron imaging are mainly its group of metabolically important radionuclides, cancer specific chemistry, and the much higher gamma-detection efficiency of coincidence collimation as compared to prior art gamma-cameras. PET's tomographic reconstruction capability has also been important clinically in describing the location of PET tracer radiation sources within the body.

Significance of PET in Breast Cancer

Statistics show that one in nine American women will be diagnosed with breast cancer. The disease kills 45,000 women each year and is the leading cause of death for women 35-50; the reported incidence of breast cancer increased by 32% from 1982 to 1987. Increased awareness has caused breast cancer to become a high profile disease in the medical community, in the news media, and with women's groups, all of whom call for better early diagnosis and treatment. There is an urgent need for improved early diagnosis in women under 35 years old.

Breast Cancer Detection in Younger Women

X-ray mammography, which images tissue density differences, is relatively ineffective for cancer diagnosis in younger women (i.e., women less than 50 years old, as in a Canadian study of 90,000 women reported in 1993). Normal breast tissue in many such women has nearly the same density as cancer ($<1\%$ difference). Furthermore, differentiating benign from malignant lesions is difficult in mammograms. Although malignant and normal cells are easily distinguished physiologically, such differences are not apparent in mammograms because they are metabolic in nature and have little effect on tissue density to x-rays. Thus, the large 1993 Canadian National Breast Screening Study (NBSS) noted above supported a conclusion that screening x-ray mammography confers no survival benefit in women ages 40-49.

In contrast, higher metabolic rates associated with the 6-13 times higher proliferation rates characteristic of malignant cells compared to normal cells are easily detected by PET with fluorine-18-deoxyglucose (FDG) and thymidine tracers. Additionally, the relatively higher metabolic rate of malignant cells is even more pronounced in younger women because breast cancer generally grows faster in such women than in older women. Hence, the natural advantage of PET over x-ray mammography in breast cancer detection is even further enhanced in younger women, where x-ray mammography is least effective. The ability to detect cancer through metabolic measurements also makes PET useful in assessing the effectiveness of chemotherapy much sooner than anatomic imaging devices, e.g., x-ray, computerized x-ray tomography, or magnetic resonance imaging.

Another advantage of PET over x-ray mammography is related to the specificity of PET screening results. About 80% of the masses detected by x-ray mammography are false positives, but cancer cannot be ruled out in these cases except by biopsy. Thus, about 500,000 fine needle biopsies (guided by ultra-sound or x-ray computed tomography) are performed annually at a cost of $1000 to $2000 per biopsy.

The diagnostic information from a properly placed biopsy is very valuable, but biopsy would not be available for the (approximately 10% of) actual tumors which are missed in routine x-ray mammography, or for the tumors which escape detection because of the x-ray shielding effect of silicone breast implants. On the other hand, PET scans with a resolution of 3-4 mm which could be administered for about $1000 to $1500 would be a substantial aid in diagnostic screening for breast cancer.

Opposing these reasons for increasing PET usage are the high price of PET cameras (ca. $2,500,000), high camera maintenance costs (ca. $250,000/year), and large space requirements for conventional PET cameras. These cost factors affect how PET may be used in screening and diagnostic studies, and the same factors would be sensitive to reductions in the size and cost of the camera itself.

Another problem in using the conventional ring form PET camera is the small axial field-of-view (typically 10-15 cm). If one wants to find cancer and its metastases throughout the body, many scans may have to be made in 10-15 cm steps (at 10-20 minutes per step). Because of the short decay half-life of most positron isotopes, such time-consuming stepping through the whole body is often difficult. To illustrate, the half-lives of commonly used radionuclides are as follows: 0-15, 2 minutes; N-13, 10 minutes; C-11, 20 minutes; F-18, 110 minutes. Even if imaging can be accomplished with these tracers, it is relatively long and the patient throughput per day is limited. Further, imaging in sequential steps only creates a snap-shot in time of a 10-15 cm cross-section; this means that tracer-uptake as a function of time for any given cross-section cannot be imaged. Hence, cancer detection is compromised because the dynamic uptake of positron tracer over time is often important for cancer imaging.

SUMMARY OF THE INVENTION

The invention comprises methods and apparatus related to improved PET cameras for imaging objects, the improvements comprising relatively small-aperture cameras with improved source localization capabilities, lower initial and maintenance costs, and both tomographic (3-D) and, in some embodiments, two-dimensional (2-D) capabilities.

The lower cost of small cameras of the present invention results primarily from reducing the number and complexity of radiation detectors in the camera, while versatility is achieved in certain embodiments by adding conformal collimators and/or by designing the cameras as hybrids, i.e., with mechanical features which facilitate imaging in two modes. First—a three-dimensional (3D) tomographic mode is included for imaging small objects, i.e. no larger than a human head, either singly or multiply (if closely spaced). In general, small object imaging with the present invention employs conformal collimators to enhance accuracy. Second—a two dimensional (2D) planar mode is included in some embodiments to simultaneously image two widely separated areas on the same object (e.g., abdomen and upper chest), or areas within two separate objects altogether. The separation function is achieved by splitting and reconfiguring the camera's gamma radiation detector array while retaining the capability for coincidence collimation.

When in the 3D mode, small PET cameras of the present invention (FIG. 1) have a plurality of gamma radiation detectors 20 arranged in stacked ring arrays, where the stack arrays have the form of a substantially right cylinder 24 (preferably a right circular or polygonal cylinder) which is disposable about an object to be imaged. These cylindrical detector arrays 24 have internal diameters of about 10 to about 25 cm.

In hybrid embodiments, the detectors are further disposed on a plurality of separable sectors comprising the right cylinder form, with each sector similar in form to a right longitudinal section of the right cylinder form, and each sector having opposing arcuate and straight edges as well as attachments for securing sectors to each other along the arcuate and straight edges. The attachments, which may be hinges having removable hinge pins, rigid interlocking attachments, or slidable attachments (as interlocking tracks or tongue-in-groove), may be disposed along straight sector edges to attach the sectors in the form of a right cylinder. In some preferred embodiments, the sectors are substantially equal in size, and there may be from two to six (preferably four) sectors. Detector arrays comprising sectors in a tomographic PET camera may be rearranged to convert the camera to a 2D configuration, with sectors positioned singly or in pairs symmetrically diametrically opposed in a substantially right cylindrical form about an object to be imaged. They may also be rearranged into curved, open planar detector arrays and positioned for coincidence detection of gamma radiation from a source between the arrays.

Right cylindrical detector arrays of the present invention, whether splittable or not, are suitable for extremities such as a hand 26. They demonstrate higher reconstructed resolution and sensitivity than arrays with larger diameters, in part because smaller size improves the signal-to-noise ratio of radiation detectors and in part because removable conformal collimators effectively reduce noise from gamma ray scattering. The collimators comprise a plurality of substantially parallel planar rings, each ring having an inside contour and an outside contour, the outside contour of each ring substantially conforming to and being insertable within the substantially right cylindrical array of radiation detectors, the inside contours of each of the planar rings substantially conforming to an object to be imaged. In some preferred embodiments, the inside contours are substantially circular. The planar rings may be constructed of lead or uranium, and are preferably about 0.5 to about 1.5 mm thick.

The small cameras may also serve specialized functions in the 2D mode, wherein the cylindrical array of radiation detectors illustrated in FIG. 1 is split into two or more sectors, as schematically illustrated in FIG. 4A. Note that the sectors from right polygonal cylinders (analogous to the right circular cylinder illustrated in FIG. 1) may be substantially flat or may comprise a plurality of substantially flat segments joined at an angle less than 180°. Applied singly or in pairs, as shown schematically in FIG. 2, the split detector sectors may be used for tasks such as measuring arterial blood concentrations of tracer isotopes for physiological modeling of tracer distribution dynamics during tomographic PET imaging of an organ or body region. In embodiments comprising substantially flat or curved shaped open planar detector array sectors, a sector may be attached to a collimator having an outer contour which conforms to the detector array shape, the collimator comprising two side shields and a plurality of substantially parallel sepia, each of the side shields and septa comprising uranium, the side shields having a thickness of about 10 to 30 mm, and the septa having a thickness of about 0.5 to about 1.5 mm. At least a portion of the outer contour of the collimator matches the substantially flat or curved shape of the gamma radiation detector array. In preferred embodiments, substantially all of the detectors arrayed in a sector would be subject to receiving radiation from a source to which the detectors were directed, the radiation passing between the substantially parallel sepia of the collimator prior to reaching the detectors.

Thus, taken together, the apparatus and methods of the present invention can: (a) significantly reduce the high cost of PET imaging through more efficient use of equipment; (b) improve imaging resolution for small objects; (c) improve gamma-detection efficiency for small objects, allowing lower radiation dosage for patients; (d) split into sectors to image 2 separate radiation sources (e.g., on the same patient or on 2 patients simultaneously) with the 2D mode; (e) sum projection images from neighboring angles to improve image quality; (f) perform limited-angle reconstruction to achieve some depth resolution to minimize out-of-section activity; and (g) quantitate tumor uptake and remove overlapping tissue background using surface contour fitting.

DETAILED DESCRIPTION OF THE DRAWINGS

Figure 1:
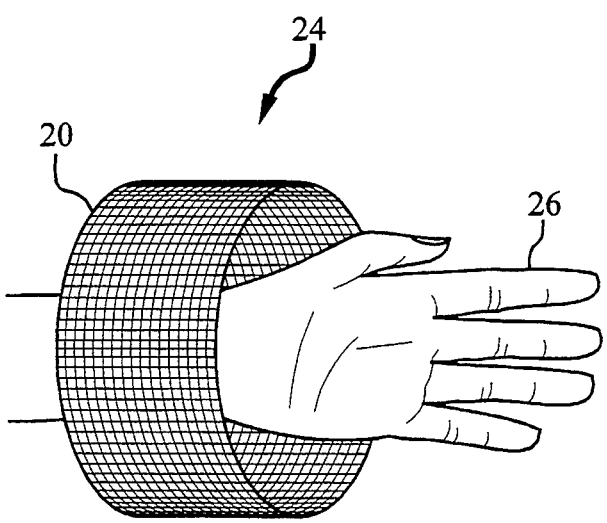
FIG. 1 is a schematic PET camera configuration for breast, brain, small animals, or extremities.
Figure 4A:
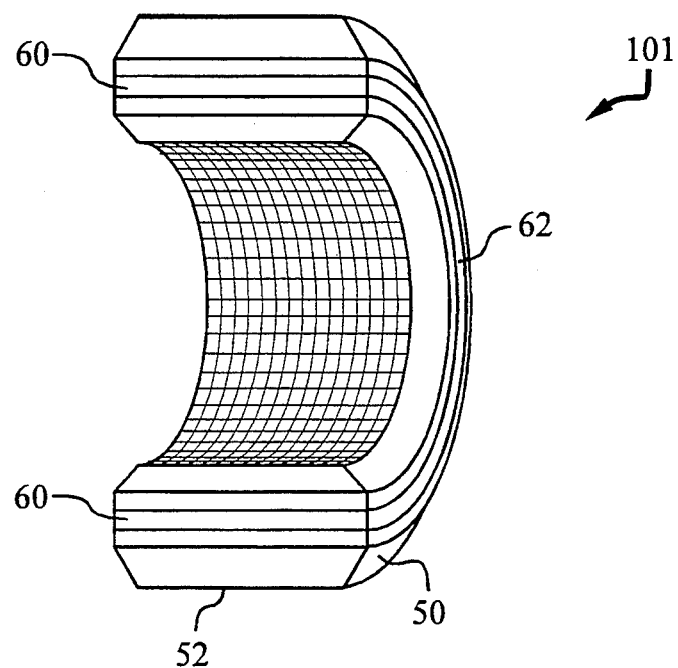

FIG. 4A schematically illustrates a split segment of the positron camera in FIG. 1 which may be used in a 2D mode.

Figure 4B:
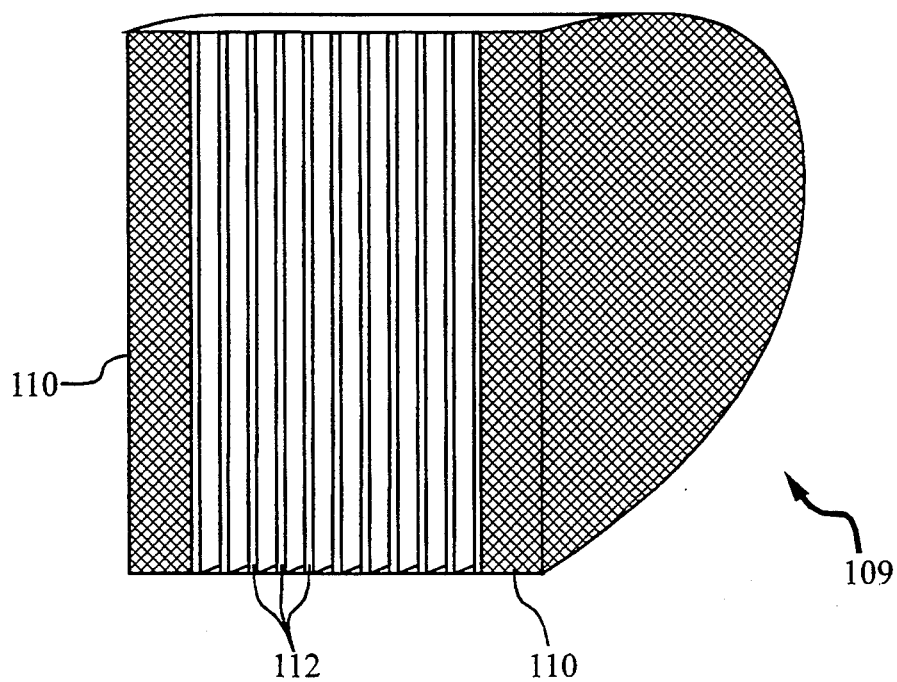

FIG. 4B schematically illustrates a detailed view of a partial-disc collimator insert for use with the split camera segment of FIG. 4A.

DETAILED DESCRIPTION

A. Definitions

C-11 carbon radionuclide with half-life of 20 minutes
2D two-dimensional or non-tomographic mode of camera operation, including partial tomography or multi-angle 2D planar imaging
3D three-dimensional or tomographic mode of camera operation
F-18 fluorine radionuclide with half-life of 110 minutes
FDG F-18-deoxyglucose, a glucose metabolic marker
N-13 nitrogen radionuclide with half-life of 10 minutes
O-15 oxygen radionuclide with half-life of 2 minutes
PET positron emission tomography

B. Detailed Description

PET Cameras in the 2D Mode

Figure 2A:
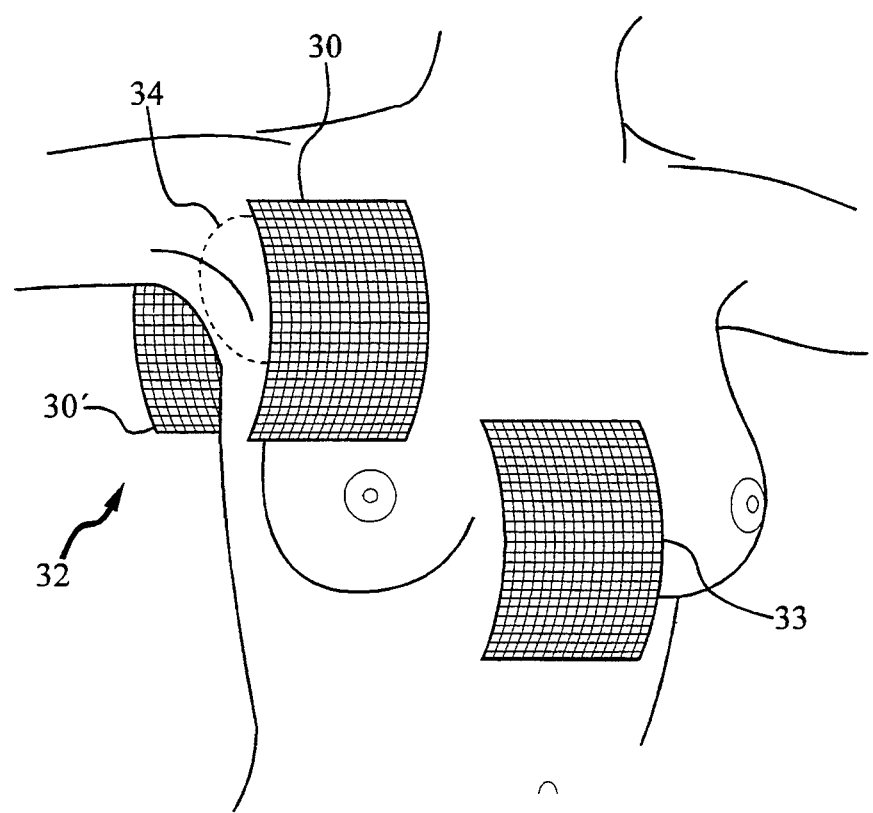
FIG. 2A illustrates coincidence detection schematically using two detector array sections on opposite sides of the body.
Figure 2B:
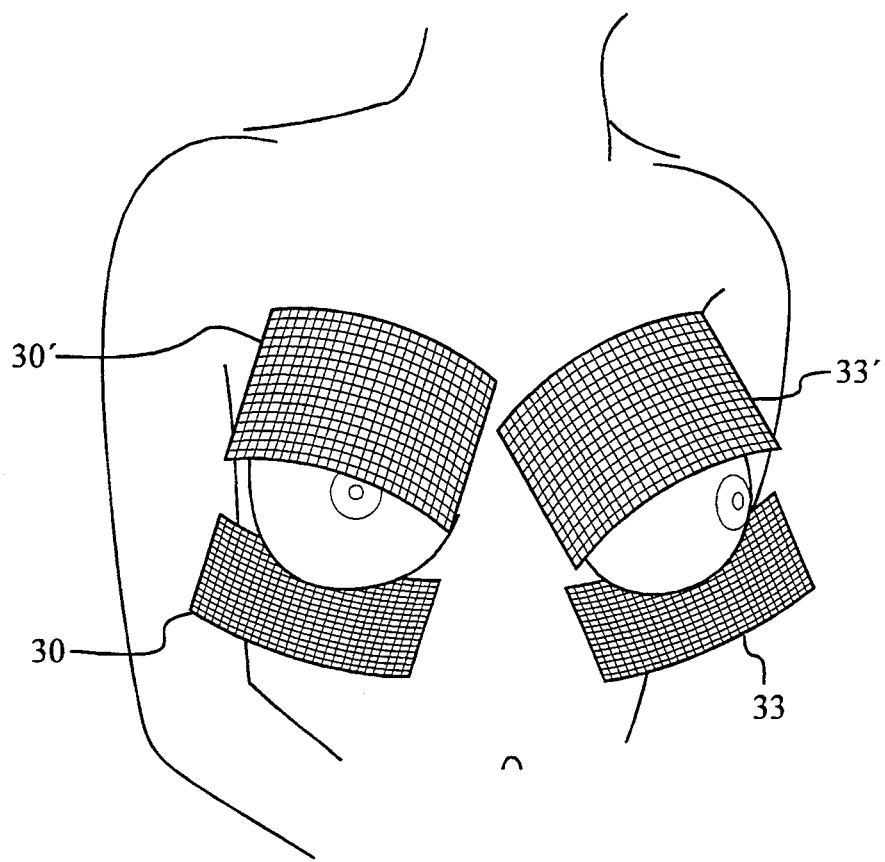
FIG. 2B illustrates coincidence detection schematically using detector array sections on opposite sides of each breast.

FIGS. 2A and 2B schematically illustrate examples of PET camera configurations of the present invention for the 2D mode (partial tomography or multi-angle 2D planar imaging). Advantages of these hybrid camera configurations are also illustrated. Consider right cylindrical (or polygonal) detector array 24 (FIG. 1) separated into four substantially identical sectors 30, 30', 33, 33' any two of which may be transformed into a pair of opposing detector arrays 32 for spot imaging a predetermined target area 34. Note that in FIG. 2A, sector 33' is not shown because it is behind the patient, being paired with sector 33 in a manner analogous to the pairing illustrated for sector 30' with sector 30.

Each sector 30, 30', 33, 33' has the form of a right longitudinal section of the right cylindrical detector array 24, and thus has opposing arcuate (or angled) and straight edges. Applications for detector array pairs 32 include: (a) detecting metastases in commonly suspected metastatic sites for better cancer staging, e.g., checking the axillary nodes on patients with confirmed primary breast cancer; (b) detecting locally recurrent tumors; (c) monitoring treatment responses for any known neoplasm; (d) locating cancer and biopsy sites in a suspected organ; and (e) measuring tumor characteristics, such as estrogen receptor status on confirmed neoplasms, for treatment planning. Note that with the four sectors 30, 30', 33, 33', both breasts can be imaged simultaneously with high sensitivity as illustrated in FIG. 2B. High sensitivity is achievable because of the sectors'-proximity to the tissue being imaged and the absence of intervening tissue which would attenuate signal strength (e.g., as the chest would attenuate signal strength from the breast in a conventional PET scan).

It should be noted that the four sectors 30, 30', 33, 33' may either be stationary, or one or both of each pair of sectors may be configured to rotate about the tissue being imaged. For example, sector pairs 30, 30' may each rotate 90° relative to the central axis of the cylinder, or sector 30 may be fixed, and sector 30' may rotate 180° relative to the central axis of the cylinder. Other possible combinations of sector rotation are also contemplated.

Small PET Cameras in the Full Tomographic Mode

When detector array sections 30, 30', 33, 33' (FIGS. 2A and 2B) are connected to form a complete ring 24 of small diameter (FIG. 1), a PET camera is formed which is better suited than current commercial PET cameras for imaging small objects such as a head, neck, breast, limb, or small animal. These cylindrical detector arrays 24 are small, preferably having internal diameters of about 10 to about 25 cm. The smaller camera provides: (a) about 4 times higher-than-conventional gamma-ray detection efficiency for most small objects (12 times breasts because the chest is not required to be between the breast and the detectors); (b) a much smaller-than-conventional detection ring ($\frac{1}{4}$ size), thus reducing the number of radiation detectors and the camera cost by about 80%; and (c) higher image resolution by minimization of errors due to the fact that the angle between the two gamma rays emerging from an annihilation event is generally not exactly 180°.

Conformal Coincidence Collimators

Figure 3A:
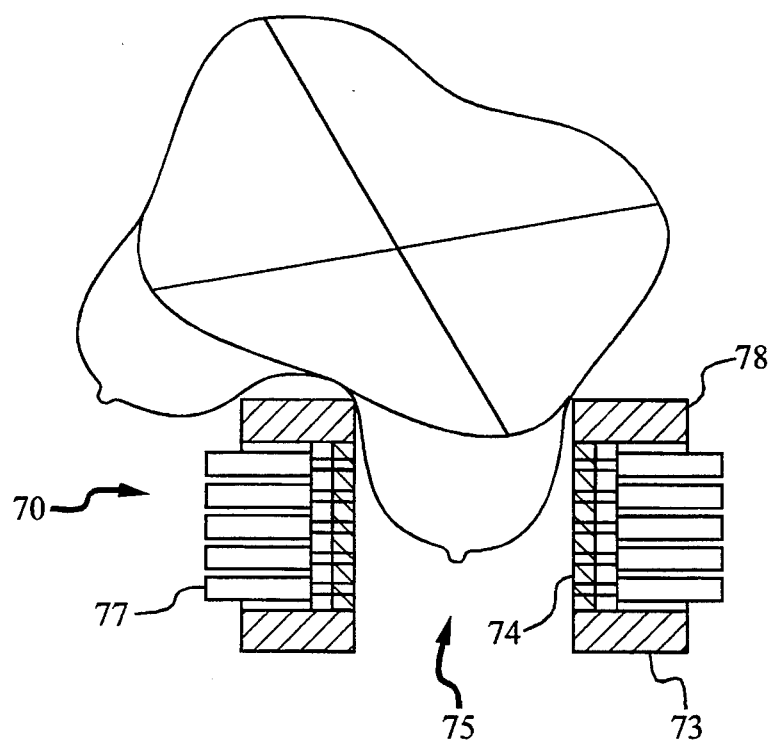
FIG. 3A is a schematic cross-sectional view of a 3D camera with a breast in position for examination with conventional shielding and collimation.
Figure 3B:
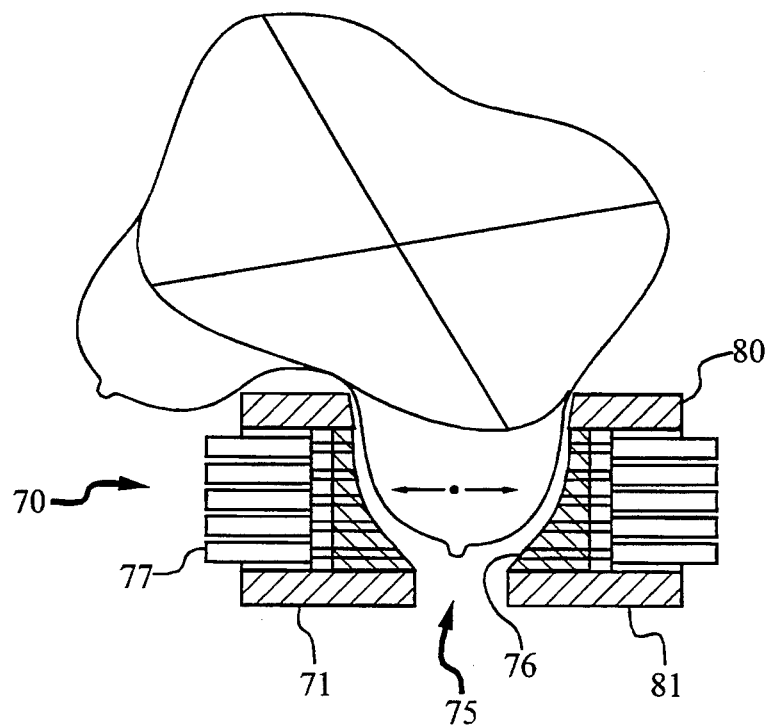
FIG. 3B is a schematic cross-sectional view of a 3D camera with a breast in position for examination with thinner uranium upper and lower collimator shields than those in FIG. 3A, and also with a conformal collimator.
Figure 3C:
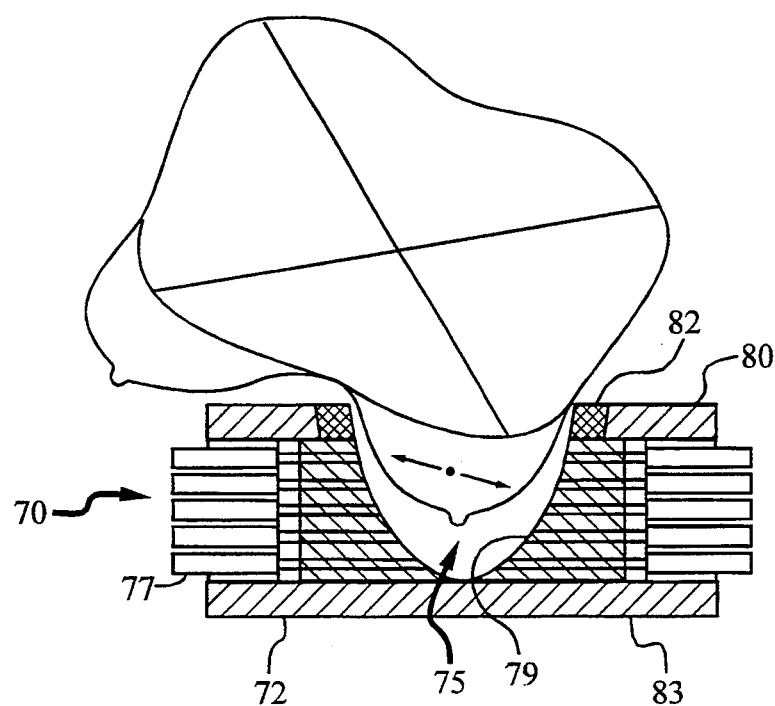
FIG. 3C is a schematic cross-sectional view of a 3D camera with a smaller breast in position for examination with a conformal collimator and an aperture-reducing insert for the upper collimator.

Coincidence collimators for small cameras of the present invention used in the 3D mode are fabricated as conforming stacks of substantially parallel planar rings; their structures are contrasted schematically in FIGS. 3B and 3C with that of a conventional coincidence collimator in FIG. 3A. The planar rings may be constructed of lead or uranium, and are preferably about 0.5 to about 1.5 mm thick. The camera detector array ring 70 (comprising detectors 77) and collimators 74, 76 and 79 are shown in longitudinal cross-section. In FIG. 3A, upper lead collimator shielding 78 and lower lead collimator shielding 73 enclose a stack of uniform inner diameter collimator rings 74. In contrast, FIGS. 3B and 3C illustrate stacks of conforming planar rings 76 and 79 which rest on contoured lower collimator shields 71 and 72. Thus, the contoured lower collimator shield and planar ring stack may be inserted into or removed from the detector array ring 70. The contoured collimator shield preferably abuts end surfaces of the detector array ring 70, as shown in FIG. 3C. A choice of inner contours for the rings 76 and 79 is provided in replacement rings, which can be easily exchanged to accommodate various shapes of objects to be imaged within the object field of the camera 75. Thus, planar collimator ring stacks of different internal sizes or shapes can be made to conform to differently shaped objects (e.g., breasts of different sizes). Further, in order to facilitate breast cancer imaging, the upper collimator shield 80 and lower collimator shields 71 and 72 are made of depleted uranium with a 511 KeV half-value-layer of 2 mm, (half that of lead). Similarly, an aperture-reducing insert 82 for the upper collimator shield 80 is also made of depleted uranium. By admitting more breast tissue within range of the radiation detectors, this design maximizes the breast tissue which can be imaged tomographically, as seen by comparing FIG. 3A with FIGS. 3B or 3C.

It is contemplated that contoured lower collimator shields 71 and 72 may be used with or without collimators 76 and 79.

For planar imaging with a partial-disc collimator (FIGS. 4A and 4B), the detector array ring 20 of FIG. 1 (or an analogous right polygonal cylindrical shape) is split into one or more sectors 101 having a substantially flat or curved planar shape. The 3D ring configuration of the camera (FIG. 1) is thus changed to the 2D configuration by employing sector pairs analogous to the sector pairs 30, 30' and 33, 33' schematically illustrated in FIG. 2. Partial-disc collimator insert 109 in FIG. 4B may be attached to (and substantially conforms to) sector 101 to reduce scatter radiation. Such a collimator comprises two side shields 110 and a plurality of septa 112. Side shields 110 and septa 112 preferably comprise lead or uranium. A collimator can improve 2D image quality in cases where the imaging region is very close to an organ such as the bladder, which is a strong source of gamma radiation which is prevented from reaching the detectors in general because it does not pass substantially parallel to the septa 112. Uranium side shields 110 preferably have a thickness of about 10 to 30 mm, and septa 112 preferably have a thickness of about 0.5 to about 1.5 mm.

Attachments Between Sectors

In hybrid embodiments, the detectors are further disposed on a plurality of separable sectors 101 comprising the right cylinder form, with each sector 101 similar in form to a right longitudinal section of the right cylinder form, and each sector 101 having opposing arcuate edges 50 and straight edges 52 as well as attachments 62 for securing sectors to each other along the arcuate edges and attachments 60 for securing sectors along the straight edges. See FIG. 4A. Attachments 60 and 62 may be hinges having removable hinge pins, rigid interlocking attachments, or slidable attachments (as interlocking tracks or tongue-in-groove). Attachments 60 may be disposed along straight sector edges 52 to attach sectors 101 in the form of a right cylinder, and attachments 62 may be disposed along arcuate edges 50 of sector 101 for stacking the sectors. In some preferred embodiments, sectors 101 are substantially equal in size, and there may be from two to six (preferably four) sectors. Detector arrays comprising sectors 101 in a tomographic PET camera may be rearranged to convert the camera to a two-dimensional planar configuration, with sectors 101 positioned singly or in pairs symmetrically diametrically opposed in a substantially right cylindrical form about an object to be imaged. They may also be rearranged into curved, open planar detector arrays and positioned for coincidence detection of gamma radiation from a source between the arrays.

Changes may be made in the construction, operation and arrangement of the various parts, elements, steps and procedures described herein without departing from the concept and scope of the invention as defined in the following claims.

What is claimed is:

1. A PET camera for imaging objects, the camera comprising:
a plurality of gamma radiation detectors forming a substantially right cylindrical array and disposable about an object to be imaged, said radiation detectors further disposed on a plurality of separable sectors comprising said substantially right cylindrical array, each sector similar in form to a right longitudinal section of said substantially right cylindrical array, and each sector having opposing arcuate and straight edges;
attachments for securing said sectors to each other along said arcuate edges and straight edges; and
removable collimators inserted within said substantially right cylindrical array, said collimators comprising a plurality of substantially parallel planar rings, each ring having an inside contour having varying cross-sections so dimensioned to substantially conform to exterior surfaces of an object to be imaged.

2. The camera of claim 1 wherein all sectors are substantially equal in size.

3. The camera of claim 2 wherein said attachments comprise connecting means for rearranging said sectors into open planar detector arrays.

4. The camera of claim 1 wherein said substantially right cylindrical array has an internal diameter from about 10 to about 25 cm.

5. The camera of claim 1 wherein the sectors are slidably attached to each other.

6. The camera of claim 1, wherein the planar rings are lead.

7. The camera, a of claim 1, wherein the planar rings are uranium.

8. The camera of claim 1, wherein the planar rings are about 0.5 to 1.5 mm thick.

9. The camera of claim 1, wherein the collimators comprise contoured collimator shields abutted to end surfaces of said substantially right cylindrical array of radiation detectors.

10. The camera of claim 9, wherein said contoured collimator shields are uranium.

11. The camera of claim 10, wherein the collimator shields are about 10 to about 30 mm thick.

12. A splittable PET camera for objects to be imaged, the camera comprising
a plurality of radiation detectors forming a substantially right cylindrical array;
said radiation detectors further disposed on pairs of sectors of said cylindrical array, each sector being similar in form to a right longitudinal section of said cylindrical array, each sector of each pair being of substantially equal size, and each sector having opposing arcuate and straight edges;
means for attaching said sectors together along said straight edges to form said substantially right cylindrical array;
wherein said sectors are disposable in pairs symmetrically diametrically opposed in said substantially right cylindrical array about an object to be imaged; and
removable collimators inserted within said substantially right cylindrical array, said collimators comprising a plurality of substantially parallel planar rings, each ring having an inside contour with varying cross-sections so dimensioned to substantially conform to exterior surfaces of an object to be imaged.

13. The camera of claim 12 wherein all sectors are substantially equal in size.

14. The camera of claim 12 wherein said attaching means comprise connecting means for rearranging said sectors into open planar detector arrays.

15. The camera of claim 12, wherein the planar rings are lead.

16. The camera of claim 12, wherein the planar rings are uranium.

17. The camera of claim 12, wherein the inside cross-sections are substantially circular.

18. The camera of claim 12, wherein the substantially parallel planar rings further comprise:
an outside contour, the outside contours of each of said plurality of rings substantially conforming to and being attachable to said sectors.

19. The camera of claim 18 wherein the planar rings are lead.

20. The camera of claim 18 wherein the planar rings are uranium.

21. The camera of claim 18 wherein the cross-sections are substantially circular.

22. A method of converting a tomographic PET camera to a two-dimensional camera, the method comprising
providing a tomographic PET camera, 's aid camera having a plurality of gamma radiation detectors arrayed as a right cylinder;
rearranging said detectors into curved, open planar detector arrays; and
positioning said planar detector arrays for coincidence detection of gamma radiation from a radiation source between said arrays.

23. The method of claim 22 further comprising attaching a collimator to each open detector array, each said collimator substantially conforming to the detector array shape and comprising two side shields and a plurality of substantially parallel septa, each of the side shields and sepia comprising uranium.

24. A PET camera for imaging objects, the camera comprising:
a plurality of gamma radiation detectors forming a substantially right cylindrical array and disposable about an object to be imaged; and
a removable collimator comprising a plurality of substantially parallel planar rings, each ring having an inside contour and being insertable within said substantially right cylindrical array of radiation detectors, the inside contours of said plurality of rings having varying cross-sections so dimensioned to substantially conform to exterior surfaces of an object to be imaged.

25. The camera of claim 24 wherein the planar rings are lead.

26. The camera of claim 24 wherein the planar rings are uranium.

27. The camera of claims 24 wherein the cross-sections are substantially circular.

* * * * *

UNITED STATES PATENT AND TRADEMARK OFFICE
CERTIFICATE OF CORRECTION

PATENT NO.     : 5,451,789

DATED          : September 19, 1995

INVENTOR(S)    : Wong et al.

It is certified that error appears in the above-identified patent and that said Letters Patent is hereby corrected as shown below:

In claim 7, column 8, line 17, delete ", a".

In claim 12, column 8, line 30, delete "comprising" and insert --comprising:-- therefor.

In claim 22, column 9, line 10, delete "'s aid" and insert --said-- therefor.

Signed and Sealed this

Twenty-sixth Day of March, 1996

Attest:

BRUCE LEHMAN

*Attesting Officer*     *Commissioner of Patents and Trademarks*